(12) United States Patent
Asafusa

(10) Patent No.: US 8,055,036 B2
(45) Date of Patent: Nov. 8, 2011

(54) ULTRASONIC DIAGNOSTIC APPARATUS AND ULTRASONIC IMAGE DISPLAY METHOD

(75) Inventor: Katsunori Asafusa, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 567 days.

(21) Appl. No.: 11/915,642

(22) PCT Filed: May 26, 2006

(86) PCT No.: PCT/JP2006/310580
§ 371 (c)(1),
(2), (4) Date: Feb. 20, 2009

(87) PCT Pub. No.: WO2006/126684
PCT Pub. Date: Nov. 30, 2006

(65) Prior Publication Data
US 2009/0299182 A1    Dec. 3, 2009

(30) Foreign Application Priority Data

May 27, 2005   (JP) .................................. 2005-155835

(51) Int. Cl.
G06K 9/36   (2006.01)
(52) U.S. Cl. ....................................... 382/128; 382/131
(58) Field of Classification Search .................. 382/128, 382/130, 131
See application file for complete search history.

(56) References Cited

U.S. PATENT DOCUMENTS

| | | | |
|---|---|---|---|
| 6,132,377 A | 10/2000 | Bolorforosh et al. | |
| 6,213,951 B1 | 4/2001 | Krishnan et al. | |
| 2001/0034485 A1* | 10/2001 | Kawagishi et al. | 600/443 |
| 2002/0147399 A1 | 10/2002 | Mao et al. | |
| 2004/0059218 A1* | 3/2004 | Kanda et al. | 600/437 |
| 2006/0173340 A1* | 8/2006 | Umemura | 600/458 |

FOREIGN PATENT DOCUMENTS

JP   1-176231   7/1989

(Continued)

OTHER PUBLICATIONS

European Search Report, dated Mar. 1, 2011, issued in corresponding European Patent Application No. 06 74 6909.

*Primary Examiner* — David V Bruce
(74) *Attorney, Agent, or Firm* — Antonelli, Terry, Stout & Kraus, LLP.

(57) ABSTRACT

An ultrasonic diagnostic apparatus preferable for creating a sharper image from the signal originating from contrast medium and the signal originating from biological tissues and an ultrasonic image display method are provided.

The ultrasonic diagnostic apparatus comprises an ultrasonic probe 10 for transmitting/receiving ultrasonic waves to/from an object to be examined, transmission means 12 for providing drive signals to ultrasonic probe 10, reception means for receiving the received signals outputted from ultrasonic probe 10, signal processing means 16 for processing the received signals outputted from the receiving means 14, image processing means 18 for constructing an ultrasonic image from the signals outputted from signal processing means 16, and display means for displaying the ultrasonic image.

Signal processing means 16 has means for detecting the signal intensity and the amount of variation with time of the received signal outputted from reception means 14 for each frequency band.

Image processing means 18 has means for distinguishing the signal of the ultrasonic image originating from the contrast medium and the signal originating from the biological tissues. The signal intensity and the amount of variation with time of the received signal obtained by transmitting/receiving ultrasonic waves to/from the object are detected for each frequency band, the signals originating from the contrast medium and the biological tissues are distinguished on the basis of the signal intensity and the quantity of variation of time for each frequency band, and an ultrasonic image is displayed.

20 Claims, 5 Drawing Sheets

FOREIGN PATENT DOCUMENTS

| | | |
|---|---|---|
| JP | 2002-176613 | 6/2002 |
| JP | 2002-176618 | 6/2002 |
| JP | 2002-238900 | 8/2002 |
| JP | 2002-360569 | 12/2002 |
| JP | 2004-208918 | 7/2004 |
| JP | 2005-95376 | 4/2005 |
| JP | 2005-318180 | 11/2005 |

* cited by examiner (A)

(B)

(C)

ULTRASONIC DIAGNOSTIC APPARATUS AND ULTRASONIC IMAGE DISPLAY METHOD

TECHNICAL FIELD

The present invention relates to an apparatus for imaging ultrasonic images as diagnostic images of an object to be examined and a display method thereof.

BACKGROUND ART

An ultrasonic diagnostic apparatus for imaging ultrasonic images for diagnosis of an object to be examined is for transmitting/receiving ultrasonic waves between the object via an ultrasonic probe, and for reconstructing ultrasonic images based on the receiving signals outputted from the ultrasonic probe.

As for such ultrasonic diagnostic apparatus, a so-called harmonic imaging method is known for imaging contrast effect of ultrasonic contrast medium (hereinafter referred to as contrast medium). For example, contrast medium is injected into an object and dispersed in the diagnostic region. When ultrasonic waves are irradiated to the dispersed contrast medium, harmonic components originating from nonlinearity of the medium contrast are generated. By detecting and imaging the generated harmonic components, diagnosis of blood vessel shape or discrimination of tissues is performed (for example, refer to Patent Document 1).

Patent Document 1: JP-A-H11-76231

Meanwhile, when ultrasonic waves are irradiated to the object to which contrast medium is injected, harmonic components not only originating from contrast medium but also originating from biological tissues of a part such as an organ are dispersed. When those harmonic components are detected and imaged, harmonic components originating from biological tissues are displayed being superimposed on the harmonic components originating from contrast medium as blind noise. Therefore, there are occasions that the contrast condition of the contrast medium cannot be grasped due to difficulty in, for example, accurate visual recognition of signals originating from the contrast medium on an ultrasonic image. The method in Patent Document 1 does not address such a problem. Moreover, since a local filter is used for eliminating second harmonic components, necessary contrast echo signals are also eliminated, whereby lowering signal intensity of the contrast echo signals and deteriorating image quality.

Given this factor, there is a need for creating sharper images of the signals originating from contrast medium and the signals originating from biological tissues. The objective of the present invention is to provide an ultrasonic diagnostic apparatus and ultrasonic image display method capable of creating shaper images from the signals originating from contrast medium and the signals originating from biological tissues.

DISCLOSURE OF THE INVENTION

In order to achieve the above-mentioned objective, the ultrasonic diagnostic apparatus of the present invention comprises:

an ultrasonic probe for transmitting/receiving ultrasonic waves to/from an object to be examined;

transmission means for providing drive signals to the ultrasonic probe;

reception means for receiving and processing the received signals outputted from the ultrasonic probe;

signal processing means for processing the received signals outputted from the reception means;

image processing means for constructing an ultrasonic image based on the outputted signals from the signal processing means; and display means for displaying the ultrasonic image, wherein:

the signal processing means comprises means for detecting signal intensity and temporal variation quantity of the received signals outputted from the receiving means for each frequency band; and the image processing means has means for discriminating between the signals originating from contrast medium and the signals originating from biological tissues of the ultrasonic image based on the signal intensity and time variation quantity, Also, the ultrasonic diagnostic apparatus of the present invention detects signal intensity and temporal variation quantity of the received signals obtained by transmitting/receiving ultrasonic waves between the objective for each frequency band, discriminates between the signals originating from contrast medium and the signals originating from the biological tissues of an ultrasonic image based on the signal intensity and time variation quantity for each frequency band, and displays the ultrasonic image.

BRIEF DESCRIPTION OF THE DIAGRAMS

BEST MODE TO CARRY OUT THE INVENTION

Figure 1:
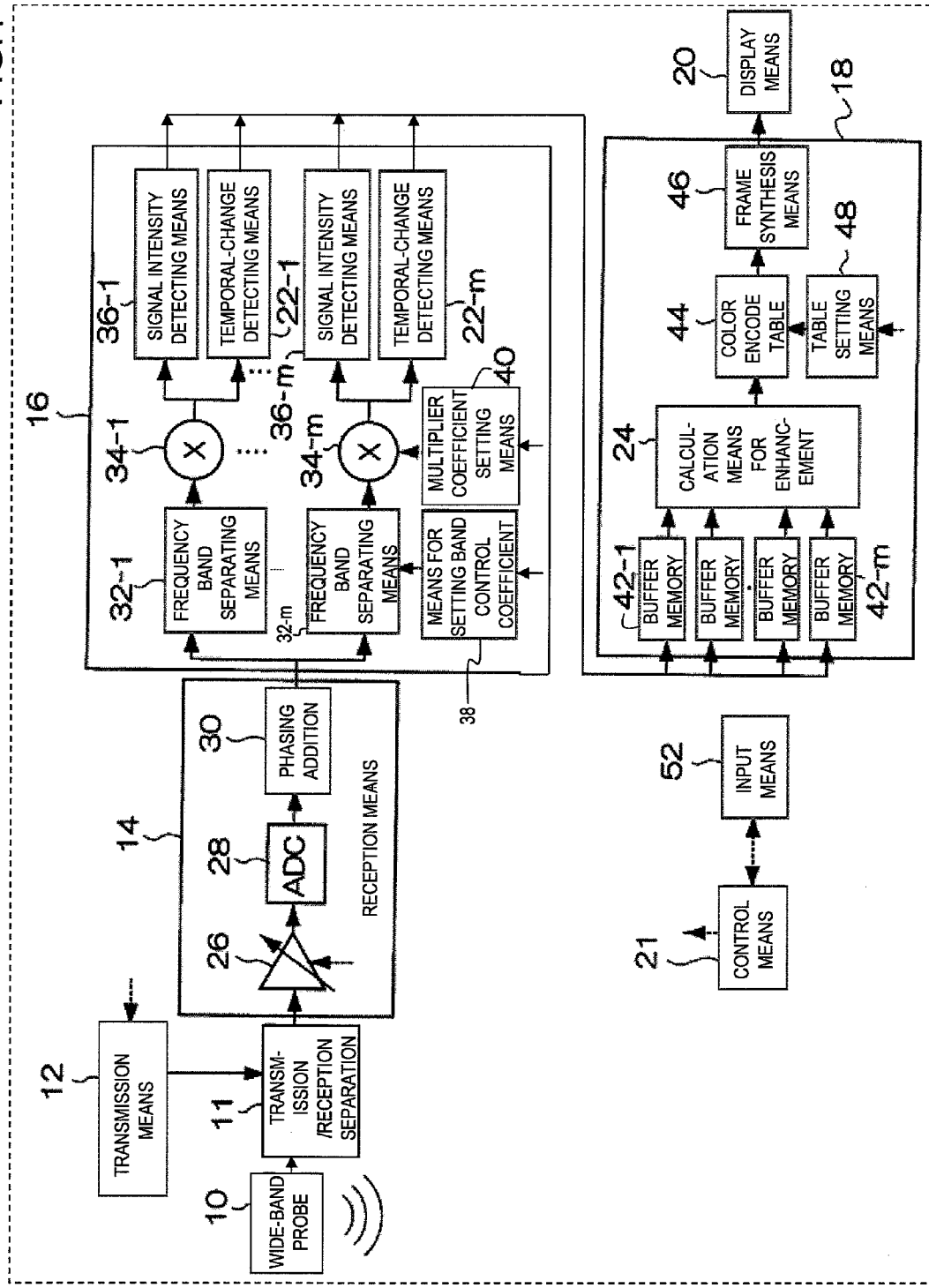
FIG. 1 is a block diagram showing the configuration of the ultrasonic diagnostic apparatus of the first embodiment to which the present invention is applied.

An embodiment of the ultrasonic diagnostic apparatus to which the present invention is applied will be described referring to the diagrams. FIG. 1 is a block diagram showing the configuration of the ultrasonic diagnostic apparatus relating to the present embodiment.

As shown in FIG. 1, the ultrasonic diagnostic apparatus comprises:

wide band probe 10 (hereinafter referred to as probe 10) for transmitting/receiving ultrasonic waves to/from an object to be examined;

transmission means 12 for providing drive signals to probe 10 via transmission/reception separating means 11;

reception means 14 for receiving and processing the received signals outputted from probe 10 via transmission/reception separating means 11;

signal processing means 16 for processing the signals outputted from reception means 14;

image processing means 18 for reconstructing an ultrasonic image based on the received signals outputted from signal processing means 16;

display means 20 for displaying the ultrasonic image outputted from image processing means 18; and control means 21 for outputting the control commands to the respective units. For the convenience of diagrammatic representation, lines indicating flow of the control commands outputted from control means 21 are omitted.

Here, signal processing means 16 for applying to the ultrasonic diagnostic apparatus of the present embodiment is provided with:

a plurality of signal intensity detecting means 36-1~36-*m* for detecting signal intensity of the received signals for each frequency band; and temporal-change detecting means 22-1~22-*m* for detecting time variation quantity based on the signal intensity and the received signals outputted from signal intensity detecting means 36-1~36-*m*. Also, image processing means 18 comprises calculating means 24 for enhancement, for enhancing the signals originating from the contrast medium and the signals originating from the biological tissues of the ultrasonic image based on the signal intensity outputted from signal intensity detecting means 36-1~36-*m* and the time variation quantity outputted from temporal-change detecting means 22-1~22-*m***.

The ultrasonic diagnostic apparatus will now be described in more details. Probe 10 is arranged with a plurality of transducers for transmitting/receiving ultrasonic waves to/from the object. As for the transducers, transducers are applied, for example, wherein a plurality of cMUT (Capacitive Micromachined Ultrasonic Transducer: IEEE Trans, Ultrason. Ferroelect. Freq. Contro. Vol. 45 pp. 678-690 May 1998) capable of controlling transceiver/receiver sensitivity are arranged. The transducers may have the composite piezoelectric structure in which a plurality of piezoelectric substances are arranged, or the multilayered structure in which piezoelectric substances having different resonance frequencies are laminated. The point is that it is desirable to apply the piezoelectric substances having, for example, more than 100% of fractional bandwidth for probe 10 of the present embodiment. Fractional bandwidth (FBW) here is represented as FBW=BW/Fc when the center frequency is set as Fc and the bandwidth is set as BW.

Reception means 14 is provided with:

amplifier 26 for amplifying the received signals outputted from probe 10 via transmission/reception separating means 11;

analogue digital converter 28 (hereinafter referred to as ADC 28) for converting the received signals outputted from amplifier 26 into digital signals; and phasing addition means 30 for executing acoustic beam focusing by performing phasing addition process with respect to the received signals outputted from ADC 28.

Signal processing means 16 comprises:

a plurality of frequency band separating means 32-1~32-*m* for extracting the received signals outputted from reception means 14** by dividing them by each frequency band;

a plurality of multiplication means 34-1~34-*m* for multiplying predetermined coefficient to the signals outputted from the respective frequency band separating means 32-1~32-*m* and perform correction in accordance with propagation time of ultrasonic waves;

a plurality of multiplication means 34-1~34-*m* for multiplying the predetermined coefficient to the signal outputted from the respective frequency band separating means 32-1~32-*m* and correcting the multiplied signal in accordance with the ultrasonic-waves propagation time;

a plurality of signal intensity detecting means 36-1~36-*m* for detecting the signal intensity outputted from the respective multiplication means 34-1~34-*m*; and a plurality of temporal change detection means 22-1~22-*m* for detecting time variation quantity of the signals outputted from the respective multiplication means 34-1~34-*m* and signal intensity detecting means 36-1~36-*m***. It also is provided with:

band control coefficient setting means 38 for setting control coefficient for the extracted band imparting to the respective frequency band separating means 32-1~32-*m*; and multiplier coefficient setting means 40 for setting multiplier coefficient for imparting to the respective multiplication means 34-1~34-*m*. In addition, counting number m is for corresponding to the numbers of the frequency band to be extracted.

Each of frequency band separating means 32-1~32-*m* has a band passing filter (BPF). Signal intensity detecting means 36-1~36-*m* is provided with means such as absolute-value calculating means or carrier-waves eliminating means. Temporal change detecting means 22-1~22-*m* have a high-pass filter or quantity survey means. As for the connection mode, for example, frequency band separating means 32-1 is connected to both signal intensity detecting means 36-1 and temporal variation detecting means 22-1 via multiplication means 34-1. While frequency band separating means 32-1 was used as a representative for explaining the connection mode, other frequency band separating means 32-2~32-*m* are also connected to signal intensity detecting means 36-2~36-*m* and temporal change detecting means 22-2~22-*m* via multiplication means 34-2~34-*m*** in the same manner.

Temporal change detecting means 22-1 detects temporal change parameters based on the received signals outputted from multiplication means 34-1 and the signal intensity inputted from signal intensity detecting means 36-1. Temporal parameters here indicate the unit time variation at ultrasonic wave repetition intervals, predetermined time variation summation quantity at ultrasonic wave repetition intervals, and predetermined time variation summation quantity at frame intervals. The ultrasonic wave repetition interval here corresponds to a cycle for repeatedly transmitting ultrasonic pulses from probe 10 with respect to the same scanning line (PRF) and may be referred to as a scanning repetition interval. The frame interval corresponds to the interval from the start of the transmission of ultrasonic pulses corresponding to the portion of one frame of the ultrasonic image to the start of the transmission of ultrasonic pulses corresponding to the next frame. While temporal change detecting means 22-1 was described as a representative, other temporal change detecting means 22-2~22-*m*** operate in the same manner.

Image processing means 18 comprises a plurality of buffer memories 42-1~42-*m* for storing the signal intensity detected by signal intensity detecting means 36-1~36-*m* and the temporal change parameter detected from temporal change detecting means 22-1~22-*m*** for each frequency band. Also, it is provided with:

calculation means 24 for enhancement as determination means for discriminating whether information of the respective pixels of the ultrasonic image is originating from the biological tissues or from the contrast medium, based on the signal intensity or temporal change parameter read out from the respective buffer memories 42-1~42-*m***;

color encoding table 44 for allocating color saturation, brightness and hue to the information of the respective pixels of the ultrasonic image based on the determination result of calculation means 24 for enhancement; and frame synthesis means 46 for constructing an ultrasonic image by synthesizing the signals outputted from color encoding table 44. It also comprises table-setting means 48 for switching color maps of color encoding table 44 or adjusting hues of color maps.

Buffer memory 42-1 here sends the signal intensity or temporal change parameter to calculation means 24 for enhancement in accordance with the control commands. For example, in accordance with the desired condition such as ultrasonic measurement condition such as scan convert or zoom, diagnosis content, image reconstruction after pausing, signal intensity information and temporal change parameters are outputted to calculation means 24 for enhancement from buffer memory 42-1 in real time or resting state for the portion of continuous frames or a number of frames at several-hundred-frame intervals. While buffer memory 42-1 was described as a representative, other buffer memories 42-2~42-$m$ operate in the same manner. As for the number of setting buffer memories 42-1~42-$m$, while an example for setting only the number corresponding to the number of the frequency band for separating the received signals is illustrated, it may be arbitrarily increased.

Calculation means 24 for enhancement comprises a processor having means such as four arithmetic operation means or comparison means. This processor is provided with:

a function, with respect to the three kinds of information of signal intensity, unit time variation and predetermined time variation summation which are the temporal variation parameters outputted from buffer memory 42-1, to perform quantity survey calculation in order to highlight or not to highlight the information on ultrasonic contrast medium or biological tissues and calculation for obtaining the ratio between signal intensity originating from the ultrasonic contrast medium and signal intensity originating from the biological tissues in accordance with the diagnosis content; and a function to allocate color display parameters such as color saturation, brightness and hue with respect to color encoding table 44 of the latter step.

Control means 21 outputs control commands to transmission means 12, reception means 14, signal processing means 16 and image processing means 18 in accordance with, for example, a command to start imaging which is outputted from input means 52. Input means 52 is configured with devices such as keyboard, mouse, switch and knob. For example, a knob is used for switching color maps or hue adjustment of table setting means 48. A switch is used for switching the kind of diagnosis.

Figure 2:
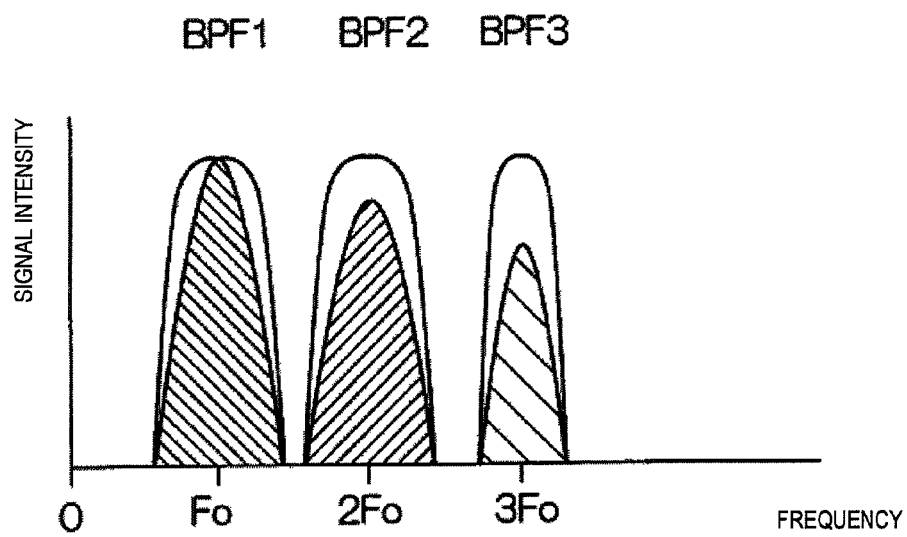
FIG. 2 shows the operation of the frequency band separating means in FIG. 1.
Figure 3:
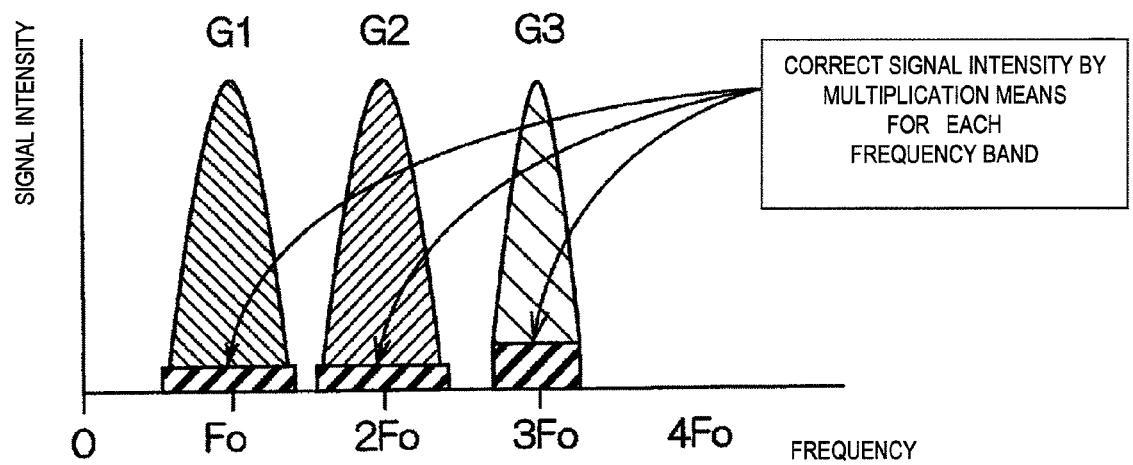
FIG. 3 is a first diagram illustrating the operation of multiplication means in FIG. 1.
Figure 4:
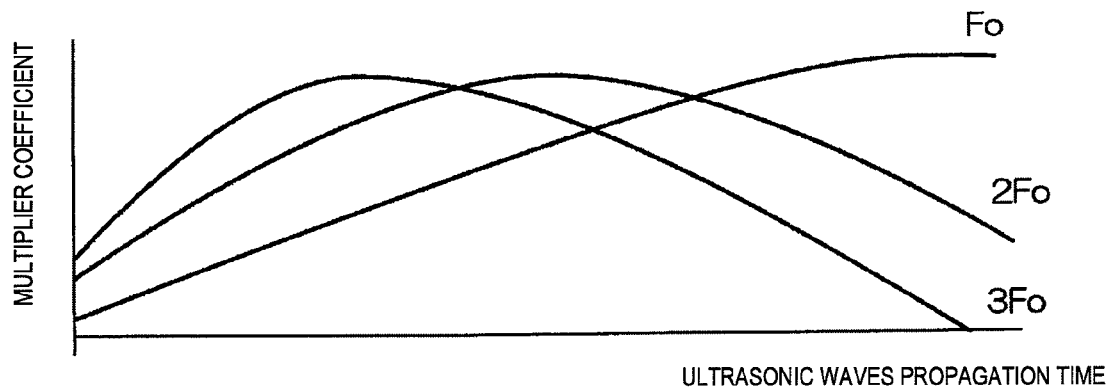
FIG. 4 is a second diagram illustrating the operation of multiplication means in FIG. 1.

The operation of such configured ultrasonic diagnostic apparatus will be described referring to FIG. 2 and FIG. 4. FIG. 2 illustrates an operation of frequency band separating means 32-1~32-$m$. FIG. 3 and FIG. 4 illustrate an operation of multiplication means 34-1~34-$m$.

First, ultrasonic contrast medium (hereinafter referred to as contrast medium) is injected into and dispersed in a diagnostic region. Then probe 10 is applied on a body surface of an object. In response to the command to start imaging, drive signals are generated by transmission means 12. When the generated drive signals are provided to probe 10 via transmission/reception separating means 11, ultrasonic waves are transmitted from probe 10 to the object. In this transmission, ultrasonic waves are transmitted from probe 10 at the lowest frequency (CF0) in a point of division (internal point) by which a bandwidth of probe 10 is approximately divided into n-numbers. One or a plurality of (for example, two) wave pulses are transmitted at ultrasonic-wave repeating intervals (PRF) with respect to the same scanning line. The wave pulses are transmitted with respect to the respective scanning lines in the same manner. The number of scanning lines are being set corresponding to the size of the imaging scope and azimuth direction resolution of the ultrasonic image.

The ultrasonic waves transmitted from probe 10 reflect as the reflected echoes in the process of being propagated in the body of the object. The reflected echo includes, other than fundamental harmonics, harmonic components originating from non-linearity of the contrast medium or harmonic components originating from the biological tissues. Such reflected echoes are received by probe 10. The received reflected echoes are outputted from probe 10 to reception means 14 as the received signals after being converted into electric signals.

The received signals inputted to reception means 14 are amplified by amplifier 26. The amplified received signals are converted into digital signals by ADC 28. The digitalized received signals are outputted from reception means 14 to signal processing means 16 after being phased and added by phasing addition means 30.

The received signals inputted to signal processing means 16 are inputted to frequency band separating means 32-1~32-$m$ respectively, and here become the received signals being separated and extracted for each setting frequency band of m-number of kinds. For example, as shown in FIG. 2, the signal corresponding to the fundamental harmonics included in the received signals (F0) is extracted by frequency band separating means 32-1. The signal corresponding to the second harmonic component included in the received signals (the signals corresponding to 2F0) is extracted by frequency band separating means 32-2. The signal corresponding to the third harmonic component included in the received signals (the signals corresponding to 3F0) is extracted by frequency band separating means 32-3. Meantime, without being limited to this pattern, in addition to extracting the high order harmonic components, intermediate frequency (for example, Sub Harmonic, 1.5 Harmonic and $3^{rd}$ Harmonic) may be extracted.

The intensity of the signals outputted from the respective frequency band separating means 32-1~32-$m$ is corrected by multiplication means 34-1~34-$m$ as shown in FIG. 3. For example, the received signal outputted from frequency band separating means 32-1 is inputted to multiplication means 34-1, the predetermined multiplier coefficient is multiplied here to the signal and the signal intensity is corrected. In the same manner, the received signal outputted from frequency-band separating means 32-2 is corrected by multiplication means 34-2, and the received signal outputted from frequency band separating means 32-3 is corrected by multiplication means 34-3 respectively.

The multiplier coefficient here is variably controlled by multiplication means 40, for example as shown in FIG. 4, with respect to the propagation time of ultrasonic waves in every frequency band that is every multiplication means 34-1~34-$m$. More concretely, as for the received signals (F0), multiplier coefficient is increased in approximate proportion to the increase of propagation time of the ultrasonic waves. As for the received signal (2F0), the multiplier coefficient is gradually increased up to the predetermined propagation time of ultrasonic waves, and after passing that time the multiplier coefficient is gradually decreased. As for the received signal (3F0), the multiplier coefficient is variably changed basically in the same manner as the case of the received signal (2F0) but the propagation time of ultrasonic waves where the multiplier coefficient reaches the maximum is shorter than the case of the received signal (F20). By variably controlling the multiplier coefficient with respect to the ultrasonic waves propagation time, lowering of the signal intensity due to the attenuation or dispersion generated in the propagation process of ultrasonic waves in the body of the object can be corrected.

The respective received signals corrected by multiplication means 34-1~34-*m* are inputted to both signal intensity detecting means 36-1~36-*m* and temporal change detecting means 22-1~22-*m*. The received signals inputted to signal intensity detecting means 36-1~36-*m* are performed with a process such as absolute value calculation or elimination process of carrier waves. Through such process, the signal intensity can be detected for each setting frequency band of m-number of kinds. The detected signal intensity is outputted to temporal change detecting means 22-1~22-*m*, and maintained in buffer memories 42-1~42-*m*.

On the other hand, in temporal change detecting means 22-1~22-*m*, temporal change parameter is detected for each set frequency band of m-number of kinds based on the received signals inputted via multiplication means 34-1~34-*m* and the signal intensity inputted from signal intensity detecting means 36-1~36-*m*. The temporal change parameters here are a unit time variation quantity at ultrasonic waves repeating intervals, predetermined time variation summation at ultrasonic waves repeating intervals and predetermined time variation summation at frame intervals. For example, when the signal intensity is set as I(t), the temporal change parameter of each frequency band can be obtained by temporal change detecting means 22-1~22-*m* as shown in chart 1. The obtained temporal change parameter is maintained in buffer memories 42-1~42-*m* for each frequency band of m-number of kinds.

CHART 1

|  |  | Temporal change parameters |
|---|---|---|
| Unit time variation | Ultrasonic wave repetition interval frequency tp | $|dI(tp)/dtp|$ |
|  | Frame interval frequency tf | $|dI(rf)/drf|$ |
| Predetermined time variation summation | Ultrasonic wave repetition interval frequency tp | $\Sigma (|dI(tp)/dtp|)$ |
|  | Frame interval frequency tf | $\Sigma (|dI(tf)/dtp|)$ |

More description of the temporal change parameters will be added here. As for the unit time variation quantity, it turns out large when the signal intensity is high and the change is drastic, and it turns out small when the signal intensity is low and the change is moderate. The predetermined time variation summation is a summation of the unit time variation quantity in a predetermined time, which turns out large when the unit time variation of the predetermined time is large and continuous, and turns out small when the unit time variation is small and occurs singly. More concretely, as for the contrast medium, static biological tissues (for example, a kidney), dynamic biological tissues (for example, a heart or blood vessel) and blood cells, the ultrasonic frequency band and time variation quantity have characteristics as shown in FIG. 2. As seen in FIG. 2, the characteristics of the contrast medium are a point that the signal intensity turns out large due to a big difference in acoustic impedance compared to the biological tissues, a point that the fundamental harmonic, second harmonic and third harmonic turn out all large since the volume change by irradiation of ultrasonic waves are non-linearly oscillated, and a point that the unit time variation quantity and predetermined time variation summation turn out large since they are comparatively movable. The characteristic of the biological tissues is that the third harmonic component is comparatively small since the volume does not change compared to the contrast medium. For example, the characteristic of static biological tissues is that while signal intensity turns out large, unit time variation quantity and predetermined time variation quantity turn out small due to their small movement. The characteristic of dynamic biological tissues is that while signal intensity turns out large, the unit time variation quantity at ultrasonic wave repetition intervals turns out comparatively small and the predetermined time variation summation at frame intervals turns out large due to their slow movement. The characteristic of blood cells is that while the signal intensity turns out smaller than the biological tissues, the unit time variation quantity and predetermined time variation summation quantity turn out larger than the static biological tissues due to their free movement within the body.

CHART 2

|  |  | Contrast medium | Blood cell | Static organism | Dynamic organism |
|---|---|---|---|---|---|
| Signal intensity | Fundamental harmonics | Large | Intermediate | Large | Large |
|  | Second harmonic component | Large | Intermediate | Large | Large |
|  | Third harmonic component | Large | Small | Small | Small |
| Unit time variation quantity | Ultrasonic wave repetition interval | Large | Intermediate | Small | Intermediate |
| Predetermined time variation summation | Ultrasonic wave repetition interval | Large | Intermediate | Small | Intermediate |
|  | Frame interval | Large | Intermediate | Small | Large |

The signal intensity or temporal variation parameters maintained in buffer memories 42-1~42-*m* are read out by calculation means 24 for enhancement. At this time, scan convert, zoom or measurement condition of ultrasonic waves are read out in accordance with desired condition such as image reconstruction after pausing. Based on the read out signal intensity or temporal change parameters, determination is made whether the information of the respective pixels of the ultrasonic image is originating from the biological tissues or from the contrast medium by calculation means 24 for enhancement. Then based on the determination result of calculation means 24 for enhancement, color saturation, brightness and hue are allocated to the information of the respective pixels of the ultrasonic image by color encoding table 44. Based on the signals outputted from color encoding table 44, an ultrasonic image is constructed by frame synthesis means 46. The constructed ultrasonic image is displayed on display means 20.

More details of the processing content of calculation means 24 for enhancement will now be described. First, the respective signals that are separated into the respective frequency bands by signal processing means 16 are the signals on which the signal originating from contrast medium and the signal originating from biological tissues are superimposed. Much the same is true on the signal of a fundamental harmonic "Sig(F0)", the signal of a second higher harmonic (2F0) and the signal of a third higher harmonic (3F0).

By calculation means 24 for enhancement, formula (1) is expressed as an arithmetic expression for enhancing the signal from medium contrast and the signal from biological tissues. A, B and C of formula (1) is the weighting factor to be multiplied to the respective signals.

$$A \cdot Sig(F0) + B \cdot Sig(2F0) + C \cdot Sig(3F0) \quad (1)$$

Based on formula (1), calculation by the signal enhancing coefficient originating from the medium contrast, calculation by the signal enhancing coefficient originating from the biological tissues and calculation without enhancement process are performed by calculation means 24 for enhancement. More concretely, medium contrast, in addition to nonlinear phenomenon due to propagation of ultrasonic waves in the elastic body, has resonance frequency from the result of hardness and inertia in accordance with the original radius of the contrast medium (For example, IEEE Ultrasonics Symposium 1996 P1451). Consequently, while the signal originating from the contrast medium has a certain degree of signal intensity in the higher harmonics of a comparatively high order, the signal originating from the biological tissues has small signal intensity in the higher harmonics of a comparatively high order. Therefore, when it is desired to highlight the signals originating from the contrast medium, formula (1) should be calculated by making the weighting coefficient as "$C \approx 1$, $A \approx B \approx 0$". When it is desired to highlight the signals originating from the biological tissues, formula (1) should be calculated by making the weighting coefficient as "$A \approx 0.5 \sim 1.0$, $B \approx 0.5 \sim 1.0$, $C \approx 0 \sim -1.0$". Summation of A, B and C here is set at a steady value (for example, "1"). Also, in the case not to implement the enhancement process, formula (1) should be calculated by making the weighting coefficient as "$C \approx A \approx B \approx 1/3$".

The calculation result (summation) of formula (1) is applied for determining the signals originating from contrast medium and the signals originating from biological tissues, by using in conjunction with the temporal change parameters in calculation means 24 for enhancement. More concretely, by performing calculation for enhancing the signals originating from the biological tissues by the signal intensity coefficient originating from the biological tissues, calculation for enhancing the signals originating from the contrast medium by the signal intensity coefficient originating from contrast medium and calculation without enhancement based on formula (1) with respect to each of the three information of the signal intensity, unit time variation quantity and predetermined time variation summation of calculation means 24 for enhancement, for example, of Sig(F0), a total of 9 signals are generated. Also, the signal intensity ratio of the signals originating from the biological tissues and the contrast medium are calculated. Such calculation process is executed on an image pixel basis.

Next, based on the 9 signals and the signal intensity ratio, color saturation, brightness or hue is allocated on an image pixel basis by color encoding table 44. For example, the signal that is not performed with enhancement process of the unit time variation quantity at ultrasonic wave repetition interval is used for the color saturation, and the hue of red is used for enhancing the contrast medium and blue is used for enhancing the biological tissues, by the signal intensity ratio between the signals originating from the biological tissues and the signals originating from the contrast medium with respect to the signal intensity. By such process, the image originating from the contrast medium is dyed in bright red, the image originating from the static biological tissues is dyed in light cobalt blue, and the image originating from the dynamic biological tissues is dyed in light blue. Such color mapping is also effective for the diagnosis of the blood vessel condition such as a tumor, as the real-time diagnosis of the vascular phase.

Also, the region dyed with contrast medium may be highlighted by simply allocating red to the signal originating from the contrast medium and blue to the signal originating from the biological tissues with respect to the signal intensity, and superimposing and color-displaying the respective signals. The point is that calculation means 24 for enhancement is to select the combination for allocating the 9 signals and the signal intensity ratio with respect to color encoding table 44. By displaying the ultrasonic image allocated with information such as color saturation by color encoding table 44, it is possible to facilitate discrimination between the image originating from the contrast medium and the image originating from the biological tissues.

Figure 5:
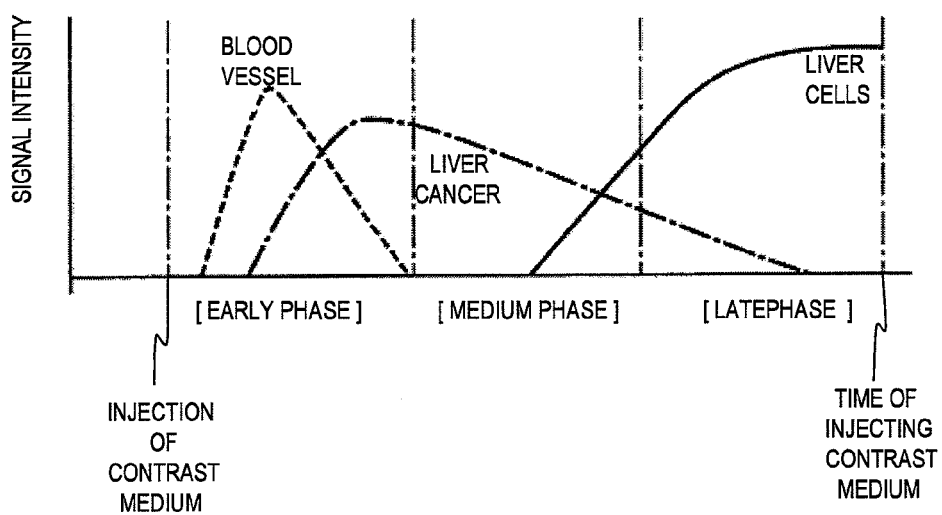
FIG. 5 shows dyeing condition of the contrast medium with respect to the elapsed time after injection of the contrast medium.

Such ultrasonic diagnostic apparatus can be applied to discrimination of tissue characterization based on the dyeing condition of the image using contract medium. Tissue characterization here means the condition, predisposition or benignancy/malignancy of the tissues. FIG. 5 is an example of the tissue differential diagnosis, and shows the dyeing condition of the image after the injection of contrast medium with respect to the elapsed time. The horizontal axis in FIG. 5 indicates the elapsed time after the injection of contrast medium, and the vertical axis indicates the signal intensity. As shown in FIG. 5, a blood vessel is dyed with contrast medium in early phase, and the rising and falling of dyeing condition of the image are precipitous. A portal starts to be dyed in the early phase later than the starting time of the blood vessel, and the rising of dyeing condition is precipitous but the falling is moderate. A liver starts to be dyed from the intermediate phase, and both rising and falling of the dyeing condition are moderate. A tumor with many new blood vessels starts to be dyed in early phase, and the falling of dyeing condition is moderate. A tumor with necrosis does not get dyed. By such dyeing mechanism, it is possible to make an effective differential diagnosis of pathologic tissues.

Differential diagnosis of the tissue characterization based on the dyeing condition of the contrast medium will be further described referring to FIG. 5 and Chart 3. Chart 3 shows the elapsed time after the injection of contrast medium into a liver and the dyeing condition of the image using contrast medium of a blood vessel, liver cell and liver cancer. The contrast medium injected into a living body is gradually circulated from the blood vessel around the whole body, and discharged outside the body over time by lung or kidney function. The contrast medium preyed by the engulfment cells, etc. stays in the body for comparatively a long time. Here, when the elapsed time from the injection of contrast medium is sectionalized into early stage, intermediate state and late stage, for example, the contrast medium intensity in the blood vessel increases drastically from the injection start time, and moderately decreases after reaching a certain time. Therefore, the unit time variation quantity, predetermined time variation summation and signal intensity summation of the signal originating from inside of the blood vessel turn out large at the early stage. Also, in the intermediate and late stage, the unit time variation quantity, predetermined time variation summation and signal intensity summation turn out small due to lowering of the intensity of contrast medium in the blood vessel.

The contrast medium intensity of the liver cell moderately increases from the intermediate stage, and stays very long time due to the prey by the engulfment cells. Consequently, the unit time variation quantity, predetermined time variation summation and signal intensity summation of the signals originating from the liver cell turn out small at the early stage.

Also, they turn out gradually larger at the intermediate stage, and reach maximum at the late stage.

Contrast medium intensity in the liver cancer drastically increases from the start time of injection at the early stage as in the same manner as the blood vessel, and drastically decreases after reaching a certain time, due to the existence of numerous new blood vessels. Consequently, the unit time variation, predetermined time variation summation and signal intensity summation of the signal originating from the liver cancer turn out large at the early stage. Also, being different from the blood vessel, the unit time variation quantity, predetermined variation summation and signal intensity summation keep a certain value in the intermediate stage since the incorrect holes existing in the new blood vessels are prone to be clogged with the contract medium. Also, the time variation quantity, predetermined time variation summation and signal intensity summation turn out small in the late stage since there is no engulfment cell. In this way, in the liver, the elapsed time after injection of the contrast medium and the dyeing condition of the contrast medium in the blood vessel, liver cell and liver cancer are different. In addition, while an example for discrimination of the tissues in the liver is described, the tissue discrimination can also be applied to the tissues of the other organs. For example, in a circulatory system, the dyeing time is different between the blood vessel flowing directly from the heart to the biological tissues and the portal passing through the small intestine. Also, there are occasions that necrosis tissues where there is no blood flow and bouton, etc. do not get dyed. In this way, by the visual recognition of the sharp image using the contrast medium, tissue characterization of the liver cell can be accurately discriminated.

may be applied to the case of static images, images once stored or abdominal examination using the on-the-fly processing.

In concrete terms, referring to FIG. 5, when attention is on the liver and the liver is colored in red at the early phase and is colored in green at the intermediate phase, it is possible to determine that the colored region thereof is a liver cancer. In particular, only the liver cancer is colored in the liver at the anterior half of the intermediate phase, it is possible to recognize the whereabouts of the liver cancer by merely observing the phase. In color encoding table 44, it is possible to display only the liver cancer region by setting so as to display only the colored region at the anterior half of the intermediate phase. Then the image created from the signal originating from the biological tissues and the image colored only in the liver cancer are superimposed by frame synthesis means 46. Through such creation of the ultrasonic waves, it is possible to identify in what region the liver cancer exists in the living body.

Figure 6:
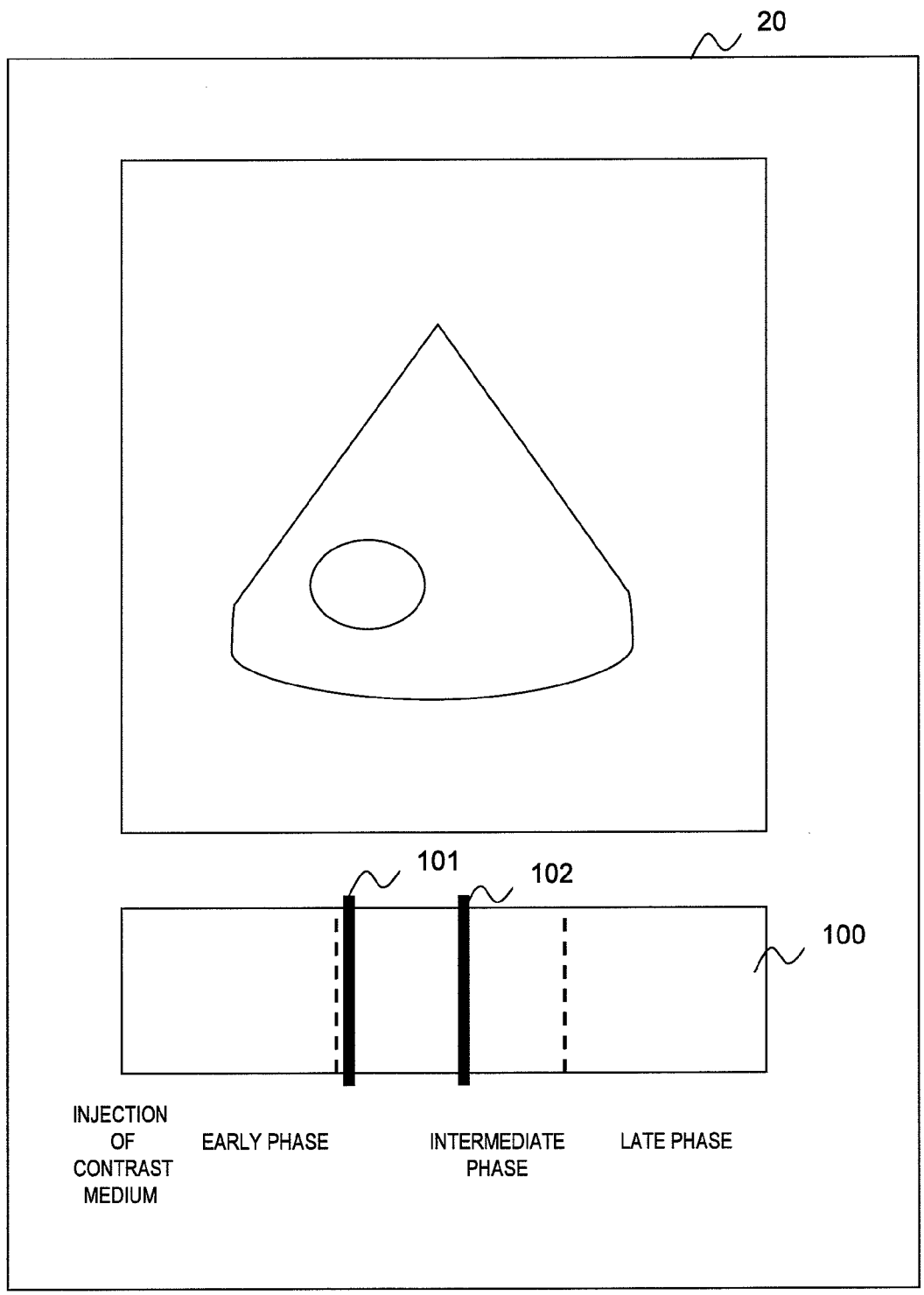
FIG. 6 shows a display range after injection of the contrast medium.

As shown in FIG. 6, bar 100 for selectively displaying the signal originating from the contrast medium is displayed on the lower part of display means 20, and the signal originating from the contrast medium is selectively displayed using input means 52. Time phase bar 100 is divided into an early phase, intermediate phase and late phase. The borderlines between these phases are indicated by a dotted line. On time phase bar 100, starting point 101 for indicating the start and ending point 102 for indicating the end are displayed. Starting point 101 and ending point 102 are operated by input device 52, the operated information is transmitted to control unit 21, and color encoding table 44 is controlled by control unit 21. Color encoding table 44 performs coloring using the signals

CHART 3

|  |  | In a blood vessel | Liver cell (engulfment cell) | Liver cancer (no neovascularity or engulfment cell) |
| --- | --- | --- | --- | --- |
| Early stage | Unit time variation | Large | Small | Large |
|  | Predetermined time variation summation | Large | Small | Large |
|  | Signal intensity summation | Large | Small | Large |
| Intermediate stage | Unit time variation | Small | Intermediate | Intermediate |
|  | Predetermined time variation summation | Small | Intermediate | Intermediate |
|  | Signal intensity summation | Small | Large | Intermediate |
| Late stage | Unit time variation | Small | Large | Small |
|  | Predetermined time variation summation | Small | Large | Small |
|  | Signal intensity summation | Small | Large | Small |

More specifically, as an example of color mapping for discriminating the tissue characterization, the coefficient is set for enhancing the contrast medium, color saturation is set for the unit time variation quantity at ultrasonic wave repetition intervals, and brightness is set for the time variation quantity at frame intervals. Then the red hue is allocated to the early phase of the elapsed time after injection of the contrast medium, green hue is allocated to the intermediate phase, and blue hue is allocated to the late phase. By doing so, the dyeing condition of the contrast medium can be determined. For example, determination can be made whether the rising and falling of the dyeing in the imaging is precipitous or not. Also, determination can be made as to whether the dyeing continues or not. Further, determination can be made as to which of the early phase, intermediate phase and late phase is being dyed with contrast medium or not dyed. On the basis of such dyeing condition, it is possible to discriminate the tissue characterization. Color mapping of the present embodiment between starting point 101 and ending point 102 that are originating from the contrast medium.

The coloring starts from the phase in which starting point 101 is displayed, and it ends at the phase in which ending point 102 is displayed. In an example of FIG. 6, it is possible to display only the liver cancer region by setting starting point 101 and ending point 102 in the anterior half of the intermediate phase so as to display only the region colored in the anterior half of the intermediate phase. When it is desired to observe only the liver cells, starting point 101 and ending point 102 are to be set in the posterior half of the late phase.

As described above, in accordance with the present embodiment, it is possible to determine whether the information of the ultrasonic image in each pixel is originating from medium contrast or from biological tissues, by extracting the time variation quantity of the received signals outputted from reception means 14 for each frequency band and detecting the intensity and time variation quantity of each signal. As a result, by enhancing and color displaying the signals originating from the contrast medium and from the biological tissues based on the determination result, each signal originating from the contrast medium and from the biological tissues can be clearly imaged.

In this way, even in the case that the discrimination of tissue characterization is performed on the basis of dyeing condition of the contrast medium, a sharper dyed-image can be obtained whereby enabling accurate tissue discrimination.

Also, the color ultrasonic image of the present embodiment may be displayed by imaging a black and white tomographic image before injecting contrast medium into an object, and juxtapose or superimpose the imaged black and white tomographic image to or on the color ultrasonic image. By doing so, the black and white tomographic image becomes the background image with respect to the color ultrasonic image whereby making it easier to carry on the procedure while visually observing the organ for diagnosis on the image.

Figure 7:
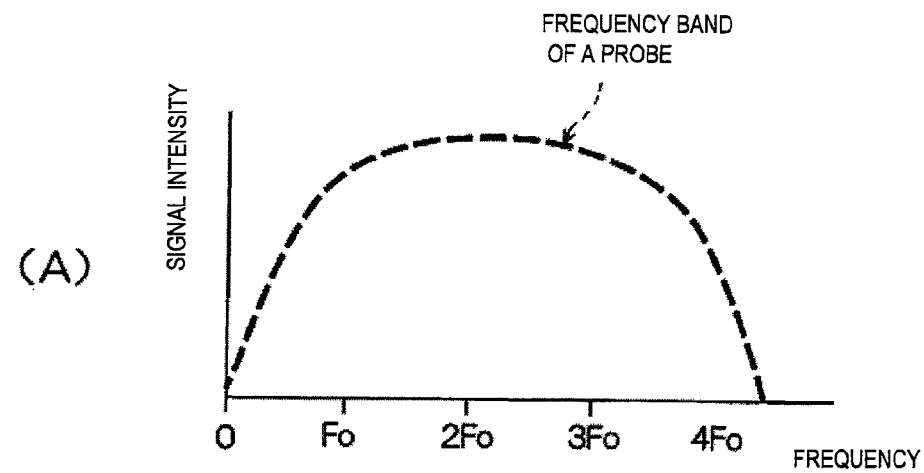
FIG. 7 illustrates frequency characteristics of the probe in FIG. 1.
Figure 7:
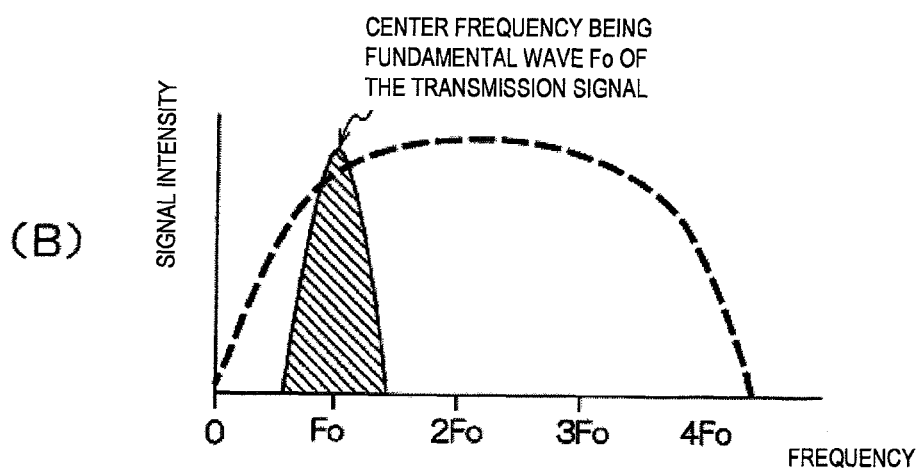
Figure 7:
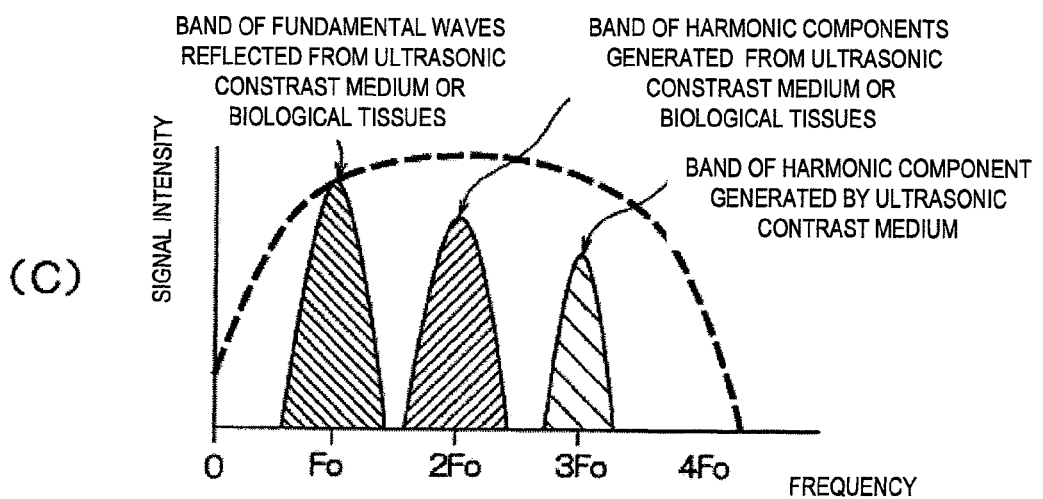

Here, probe 10 of the present embodiment will be described in detail. Since the probe having, for example, more than 100% of fractional bandwidth is used for probe 10 of the present embodiment, even higher harmonics of comparatively high order can be received with high sensitivity. This point will be explained referring to FIG. 7. FIG. 7A shows the frequency band characteristics of probe 10 relating to the present embodiment by a dotted line. FIG. 7B shows the frequency band of the ultrasonic wave transmitted from probe 10. FIG. 7C shows the frequency band of the ultrasonic wave received from probe 10. The horizontal line of FIG. 7 denotes the frequency, and the vertical line denotes the signal intensity. The frequency band is denoted as lower band F0, central band 2F0 and higher band 3F0.

First, as comparison with the present embodiment, the case of the probe arrayed with transducers formed with PZT (piezoelectric zirconate titanate) will be described. This probe has degree of 60%~80% of fractional bandwidth, thus has the frequency band in the case, for example, that the center frequency if 5 MHz, from 3 MHz of lower band frequency to 7 MHz of higher frequency. Here, if the ultrasonic-wave transmitting frequency is set as 3 MHz, the second higher harmonic is 6 MHz and the third higher harmonic is 9 MHz. However, since the third higher harmonic 9 MHz is more than 7 MHz of the high-pass frequency of the probe that is out of its frequency band, there are cases that the sensitivity is drastically lowered. Also, though a method is available to receive higher harmonics within the frequency band by setting the transmission frequency at a lower frequency that is, for example, 2 MHz and setting the second higher harmonic as 4 MHz and the third higher harmonic as 6 MHz, it can be a cause of inefficiency since the transmission frequency is out of the frequency band.

In this regard, since probe 10 of the present embodiment has more than 100% of fractional bandwidth, when the central frequency is, for example, 5 MHz, the frequency band will be from 2.5 MHz of the low-pass frequency to 7.5 MHz of the high-pass frequency. Here, if transmission frequency (F0) of probe 10 is set as 2.5 MHz as shown in FIG. 7B, the higher components can be received within the frequency band with second higher harmonic (2F0) being 5 MHz and third higher harmonics (3F0) being 7.5 MHz as shown in FIG. 7C. In other words, fundamental harmonics band originating from the contrast medium or from the biological tissues and the signal of the higher harmonic band originating from the contrast medium or the biological tissues can be received with high sensitivity.

In conclusion, since it is possible to receive even higher harmonics of comparatively high order, it is possible to create sharper images of the signals originating from the contrast medium or from the biological tissues.

The invention claimed is:

1. An ultrasonic diagnostic apparatus comprising:
an ultrasonic probe for transmitting/receiving ultrasonic waves over a predetermined period of time between an object into which contrast medium is injected;
transmission means for providing drive signals to the ultrasonic probe;
reception means for receiving and processing the received signals outputted from the ultrasonic probe;
signal processing means for processing the received signals outputted from the reception means;
image processing means for constructing an ultrasonic image based on the signals outputted from the signal processing means; and
display means for displaying the ultrasonic image,
wherein:
the signal processing means has means for detecting signal intensity and time variation quantity of the received signals outputted from the reception means for each frequency band, and
the image processing means has means for determining whether the received signal is originating from the contrast medium or from the biological tissues based on the signal intensity and the time variation quantity of the received signal.

2. The ultrasonic diagnostic apparatus according to claim 1, wherein the image processing means allocates a hue different from the signal originating from the biological tissues to the ultrasonic image of the signal originating from the contrast medium based on the elapsed time after an injection of the contrast medium, and displays the image on the display means.

3. The ultrasonic diagnostic apparatus according to claim 1, wherein the image processing means comprises a plurality of buffer memories for storing the signal intensity and time variation quantity detected by the signal processing means for each frequency band.

4. The ultrasonic diagnostic apparatus according to claim 1, wherein the image processing means comprises calculating means for enhancement, for determining the signal originating from the contrast medium and the signal originating from the biological tissues for each pixel of the ultrasonic image for each frequency band, based on the signal intensity and time variation quantity of the received signals.

5. The ultrasonic diagnostic apparatus according to claim 4, wherein the image processing means has a color encoding table for allocating at least one of color saturation, brightness and hue to the information of each pixel on the ultrasonic image, based on the determination result of the calculation means for enhancement.

6. The ultrasonic diagnostic apparatus according to claim 4, wherein:
the calculation means for enhancement determines the dyeing condition of the contrast medium for each set phase since the time of injecting the contrast medium; and
the color encoding table updates at least one of the color saturation, brightness and hue at each determination process performed by the calculation means for enhancement.

7. The ultrasonic diagnostic apparatus according to claim 3, characterized in that the image processing means allocates the first hue to the early phase in the elapsed time after the injection of contrast medium, the second hue to the intermediate phase and the third hue to the late phase with respect to the ultrasonic image of the signals originating from the contrast medium, and displays the image on the display means.

8. The ultrasonic diagnostic apparatus according to claim 3, characterized in comprising determination means for determining whether the information of the respective pixels of an ultrasonic image is originating from the biological tissues or from the contrast medium, based on the signal intensity or temporal change parameters read out from the plurality of buffer memories.

9. The ultrasonic diagnostic apparatus according to claim 8, wherein the image processing means images a black and white tomographic image before the injection of contrast medium into the object, and juxtaposes or superimposes the black and white tomographic image on or to a color ultrasonic image.

10. The ultrasonic diagnostic apparatus according to claim 1, wherein the signal processing means has temporal change detecting means for detecting the temporal change parameters which are a unit time variation quantity at ultrasonic-wave repetition intervals, predetermined time variation summation at ultrasonic-wave repetition intervals and predetermined time variation summation at frame intervals.

11. The ultrasonic diagnostic apparatus according to claim 1, wherein the signal processing means detects, as the time variation quantity, at least one of the unit time variation quantity and the time variation quantity of predetermined time which is longer than the unit time variation thereof.

12. The ultrasonic diagnostic apparatus according to claim 1, wherein the signal processing means detects, as the time variation quantity, at least one of the time variation quantity at ultrasonic-wave repetition intervals and the time variation quantity at frame intervals.

13. The ultrasonic diagnostic apparatus according to claim 1, wherein the signal processing means has:
a plurality of frequency band separating means for extracting the received signals outputted from the reception means by dividing them by frequency bands;
a plurality of multiplication means for correcting the signals outputted from the respective frequency band separating means in accordance with the ultrasonic-wave propagation time;
signal intensity detecting means for detecting the intensity of the signal outputted from the respective multiplication means; and
temporal change detecting means for obtaining the time variation quantity based on the signals outputted from the multiplication means and the signal intensity outputted from the signal intensity detecting means.

14. The ultrasonic diagnostic apparatus according to claim 13, wherein the multiplication means variably controls for each frequency band.

15. The ultrasonic diagnostic apparatus according to claim 13, wherein the multiplication means changes weighting function, in the case of enhancing the signals originating from the biological tissues or from the contrast medium.

16. The ultrasonic diagnostic apparatus according to claim 1, wherein the ultrasonic probe has comparison ratio that is larger than 100%.

17. The ultrasonic diagnostic apparatus according to claim 1, wherein the ultrasonic probe is configured with transducers by cMUT.

18. The ultrasonic diagnostic apparatus according to claim 1, comprising a plurality of frequency band separating means for extracting the received signals by dividing them by frequency bands, characterized in that each of them has a band pass filter.

19. The ultrasonic diagnostic apparatus according to claim 2, wherein the image processing means has selecting means for selecting the signals originating from the contrast medium to be displayed on display means in the elapsed time.

20. An ultrasonic image display means characterized in:
detecting the signal intensity and time variation quantity of the received signals obtained by transmitting/receiving ultrasonic waves between an object for each frequency band;
determining the signal originating from contrast medium and from biological tissues of an ultrasonic image based on the signal intensity and time variation quantity for each frequency band; and
displaying the ultrasonic image.

* * * * *